United States Patent [19]
Reed

[11] Patent Number: 5,479,293
[45] Date of Patent: Dec. 26, 1995

[54] PORTABLE MAGNIFICATION APPARATUS FOR CONDUCTING MEDICAL EXAMINATIONS

[76] Inventor: Theodore P. Reed, 4361 Baildon Rd., Trappe, Md. 21673

[21] Appl. No.: 298,312

[22] Filed: Sep. 1, 1994

Related U.S. Application Data

[63] Continuation-in-part of Ser. No. 249,701, May 26, 1994, abandoned.

[51] Int. Cl.⁶ ............................................. G02B 23/00
[52] U.S. Cl. .................... 359/432; 359/409; 359/420; 359/421
[58] Field of Search ................... 359/399, 407, 359/409–414, 479–482, 815–816, 420–422, 432; 351/41, 57, 158, 201, 205, 221

[56] References Cited

U.S. PATENT DOCUMENTS

| | | | |
|---|---|---|---|
| 4,274,128 | 6/1981 | Malis | 359/482 |
| 4,488,790 | 12/1984 | Beecher | 359/407 |
| 4,637,696 | 1/1987 | Wilkins | 351/158 |
| 4,886,340 | 12/1989 | Kanda | 359/411 |
| 5,249,002 | 9/1993 | Chou et al. | 351/158 |

FOREIGN PATENT DOCUMENTS

49008  8/1990  United Kingdom ................... 359/411

OTHER PUBLICATIONS

"Beecher Mirage" binocular system brochure published by Beecher Research Company—2 pages.

Primary Examiner—Thong Q. Nguyen
Attorney, Agent, or Firm—Breiner & Breiner

[57] ABSTRACT

A portable apparatus useful for close range physical examinations, in particular for use as a colposcope, is described. The portable apparatus includes a stereoscopic optical unit, a main frame lens holder, an auxiliary frame lens holder, a light and mount therefor, a filter and mount therefor, and support structure which allows the component parts to be maintained in precise optical alignment and allows the apparatus to be worn by a user in the manner of eyeglasses. These components are constructed and arranged to provide for an undistorted short focal length and magnification as necessary for clear close range visualization of body tissue. The apparatus provides for increased magnification so that visualization of blood vessels and the like can be readily discerned without the need for bulky expensive equipment. This allows for screening and earlier diagnosis in a time and cost efficient manner.

9 Claims, 3 Drawing Sheets

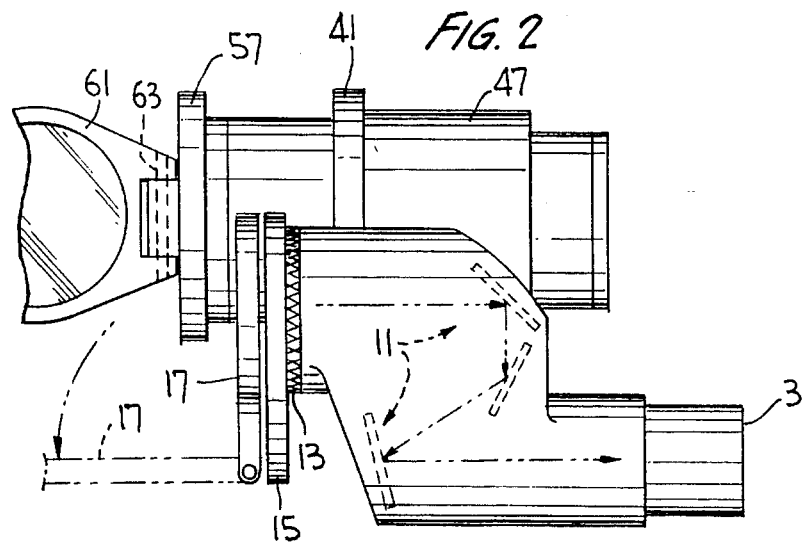
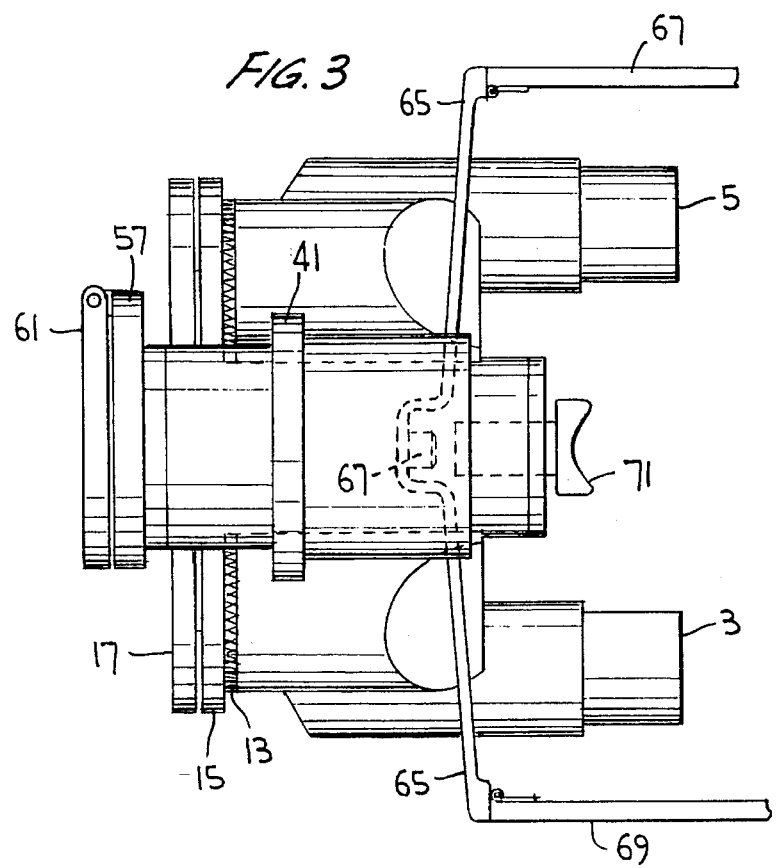
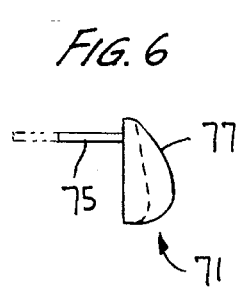

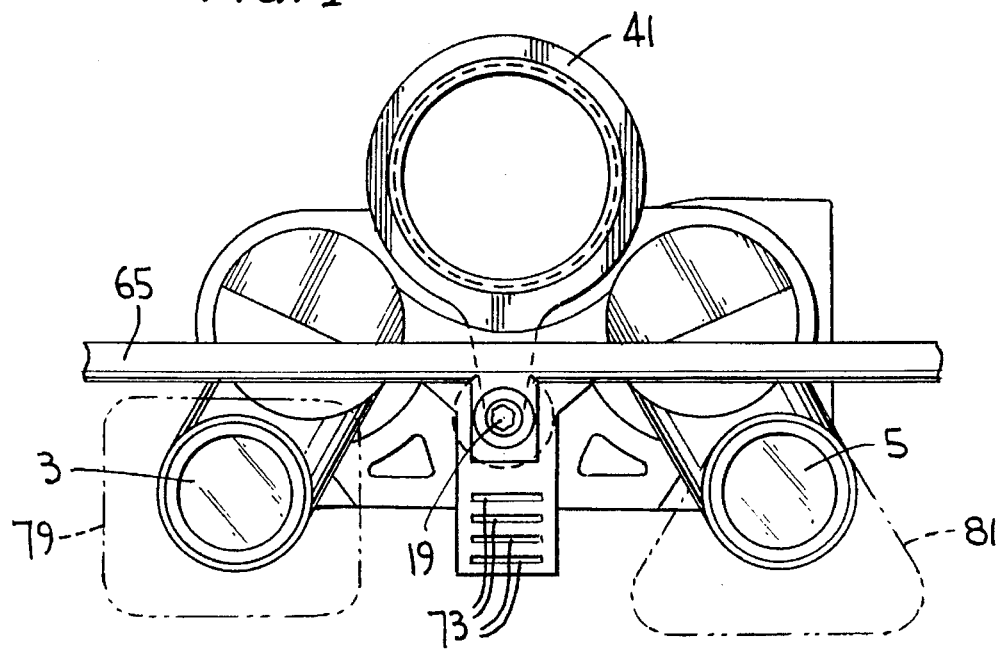
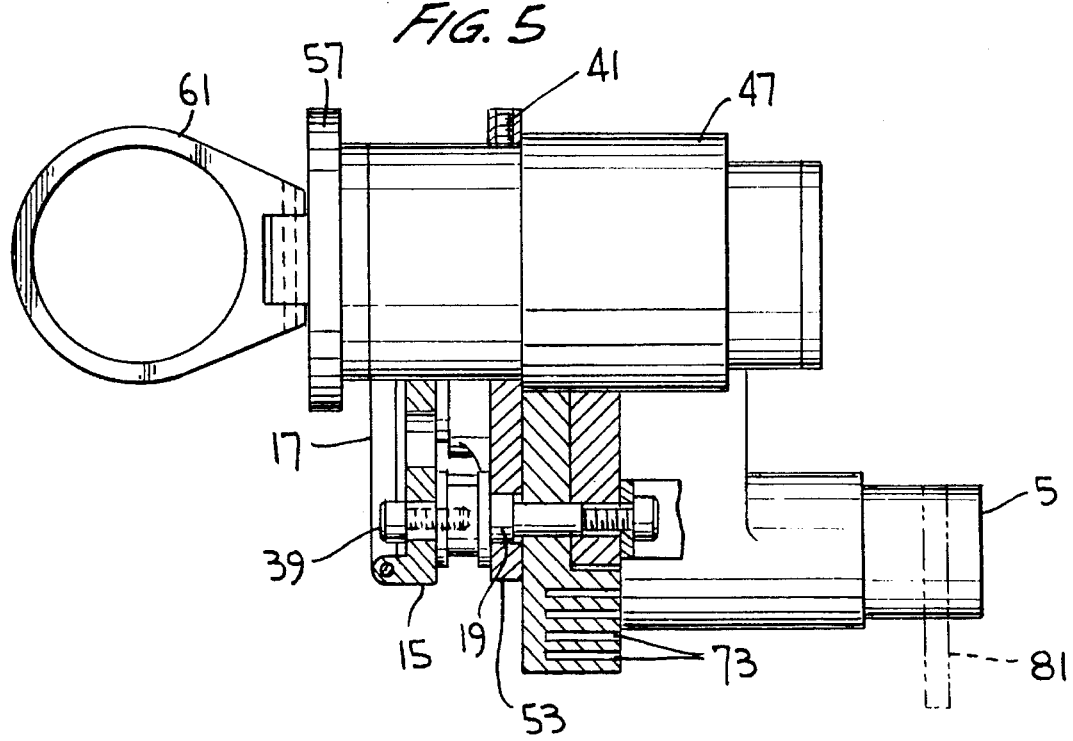

PORTABLE MAGNIFICATION APPARATUS FOR CONDUCTING MEDICAL EXAMINATIONS

RELATED APPLICATION

The present application is a continuation-in-part application of U.S. Ser. No. 08/249,701 filed May 26, 1994 now abandoned.

FIELD OF THE INVENTION

The present invention is directed to an apparatus which is portable and readily available for conducting close range physical medical examinations, in particular for use as a colposcope in conducting gynecological examinations. The portable apparatus is structured to be worn in use by a user in the manner of eyeglasses.

BACKGROUND OF THE INVENTION

In close medical examinations, in particular in the nature of colposcopy, high magnification at short working distances is required to provide an accurate or useful visual examination, i.e., magnification in the nature of 6× to 10× or higher. Conventional commercially available colposcopes are large free-standing instruments which are not readily movable due to size. Conventional colposcopes generally cost in the range of from about $4,000–$20,000 and provide magnification in the range of 6× to 40×. However, the structure of conventional free-standing colposcopes is disadvantageous in that, due to its size, it must be maintained in one location, i.e., one examination room. Further, generally due to cost, a colposcope is shared by multiple doctors. Accordingly, when a colposcopic examination is required, the patient has to be brought to the colposcope. Based on the limited availability of the colposcope, a special appointment time separate from the initial appointment is usually required resulting in additional time and cost to a patient as well as delayed examination. Thus, also, the use of a conventional colposcope as a screening tool is inhibited.

The need, therefore, for a portable magnification apparatus useful as a colposcope is present. A portable colposcopic apparatus would allow for the ready use of the apparatus as a screening tool, thereby increasing the opportunity for diagnosis and treatment. However, known portable magnifying visual apparatus do not allow for adequate magnification which provides an accurate physical examination at close range, such as necessary in the examination of body tissues at a level provided by a colposcope.

For example, U.S. Pat. No. 3,945,712 describes an opthalmoscope and magnifier worn in the manner of eyeglasses. The described opthalmoscope/magnifier utilizes mirrors in order to provide a desired field of vision through the instrument. Depending on the field of vision sought, magnification can be provided or not. Satisfactory magnification for a working distance of 12 inches is described as being from 2× to 4×.

Additionally, U.S. Pat. No. 4,195,918 describes spectacles which can have neutral or prescription lenses in combination with a light means and a magnifying zoom lens. The combined device is described as allowing for the exploration of a field of operation. Working distances of 250–350 mm are described as being provided by the spectacles. The magnification capability of the zoom lens is not set forth, but in view of the structure disclosed, low magnification only would be provided. High magnifications would result in distortions.

Additionally, U.S. Pat. No. 4,834,525 describes spectacles with lenses, which can be prescription lenses, including mounting means for receiving telescopic devices. The telescopic devices can have a binocular focus at a magnification suited to pre-determined working distances. The '525 patent recognizes that working distances will vary depending on the specific use of the spectacles. Beyond this generalization, no specific teaching is set forth regarding the magnification capabilities and working distances. The spectacles described are in the manner of loupes known in the art but having quick release mounts to allow for interchanging different telescopic devices.

Further, magnifying eyeglasses are commercially available for individuals with impaired vision, such as sold under the name "Beecher Mirage" by Beecher Research Company, Schaumberg, Ill. The glasses are monocular or binocular and have a support means positionable on a user's ears so that the glasses can be worn in the manner of conventional eyeglasses. The binocular or monocular lenses allow for improved vision close up or at a distance. The glasses use an internal mirror system and are available in strengths of 4×20, 7×30 and 10×35. In use at high magnifications at close ranges, however, these glasses have a distorted short focal length. Patents disclosing various aspects of the Beecher binocular structure including the mirror or focusing system, mounting means and the like, include U.S. Pat. Nos. 3,918, 792; 3,981,021; 3,985,421; 4,140,567; 4,140,568; 4,272, 153; 4,488,790; 4,568,154; 4,758,077; 4,779,965; 4,877,318 and U.S. Pat. No. Des. 249,350.

Accordingly, a portable apparatus, in particular worn in the manner of eyeglasses which allow for close-up visual medical examinations would be advantageous in view of the improved opportunity to readily provide examination as needed without relocation of the patient or providing a separate appointment time. Such apparatus would be readily useable and economical, thereby making diagnosis and treatment more readily available and cost efficient.

OBJECTS OF THE INVENTION

Therefore, a primary object of the present invention is to provide a portable apparatus suitable for close range visual medical examinations at undistorted short focal lengths, in particular where the portable apparatus is worn in the manner of conventional eyeglasses.

Another object of the present invention is to provide a portable apparatus suitable for close range medical examinations which are stereoscopic and include features to maintain proper optical alignment and which make the apparatus suitable for use in colposcopic examinations.

Another primary object of the present invention is to provide a portable apparatus which can incorporate prescription lenses of the user so the apparatus does not have to be removed if the object to be viewed changes.

BRIEF DESCRIPTION OF INVENTION

The present invention is directed to a portable apparatus suitable for use in conducting close range physical medical examinations, in particular in the manner of a colposcope. The portable apparatus allows for ready use regardless of patient location. Adjustments to different conditions are easily made based on the compact structure of the apparatus.

The portable apparatus is constructed and arranged to be worn in the manner of eyeglasses on the face of a user and includes a stereoscopic optical unit having a pair of viewing lenses with corresponding eyepieces and an internal mirror system; distortion correcting and magnifying lenses mounted in a main frame and auxiliary frame attached to the stereoscopic optical unit; a light means; a filter means; and a support system. The components are arranged and structured to allow for repeated optical alignment and integrity, thereby insuring consistent accurate viewing at close range with magnification.

The stereoscopic optical unit is a binocular unit with an individual S-curve mirror system present between each eyepiece and corresponding viewing lens. The eyepieces can be made to the optical prescription of a user of the portable apparatus. An adjustable focus means is present in relation to each viewing lens. A monocular system does not provide sufficient clarity and accuracy for close range medical examinations.

Attached to the viewing lenses of the binocular unit is a main frame for holding a first set of lenses which correct the distortion of the short focal length of the stereoscopic optical unit and provides a pre-determined magnification. In a portable apparatus having use as a colposcope, the preferred magnification of the lenses positioned in the main frame are 7×.

Hingedly connected to the main frame is an auxiliary frame for holding a second set of lenses. The second set of lenses provides in conjunction with the first set of lenses in the main frame a magnification of 10×. The auxiliary frame and main frame are hingedly joined to allow for the selective use of the 7× or 10× lenses in order to adjust to different needs during medical examinations. The main frame and auxiliary frame are rigidly held together so that a recurring fixed positioning of the lenses is achieved to maintain proper optical alignment. Precise optical alignment is required to insure accurate magnified viewing at a short focal length without distortion.

A mounting means is provided to hold a light means in a fixed relation to the lenses. The light means enhances visual clarity during use of the portable apparatus. Preferably, the mounting means is bendable to allow for angling of a light beam so that it coincides with the point of focus in the field of view. A mounting base component is attached to the light emitting end of the light. A filter holder is hingedly connected to the mounting base to allow a filter held within the holder to rotate into or out of the light beam as desired. When the portable apparatus of the invention is used as a colposcope, the filter is green. For example, when the apparatus is used as a colposcope to examine a woman's vagina, cervix or vulva following the return of an abnormal pap smear, examination of the blood vessels is carried out. The use of a green filter with a light source allows for improved visualization of the blood vessels during examination. A suitable switch/power means is connected to the light to control the operation of the light. A suitable source of power is a battery or a 110 V AC battery with a small transformer connected to the light.

To maintain the components of the portable apparatus in operative relation to each other, which is essential to maintaining proper optical alignment, a single mounting stud element is used as part of the support system for the apparatus. The mounting stud passes through the main frame lens holder, the light mounting means, the stereoscopic optical unit and, preferably, a portion of the support system which is attached to ear prongs which allow the apparatus to be worn in the manner of eyeglasses. The stereoscopic optical unit preferably also includes a nose piece in the base of the stereoscopic optical unit. The nose piece provides support, comfort, and weight distribution. The nose piece operates in conjunction with the ear prongs to support the apparatus on the face of a user. A head band can be attached to the ends of the ear prongs, if desired, to provide added security.

In an alternative embodiment, regular prescription eyeglass lenses can be mounted adjacent or surrounding the eyepieces of the stereoscopic optical unit so that, if neutral vision is required, the portable apparatus does not have to be removed from a user's head but the line of vision of the user's eyes simply redirected and/or apparatus slightly adjusted in position on the face of the user.

The portable apparatus of the invention has been found, through comparison studies performed with a conventional free-standing colposcope, to provide essentially equivalent diagnostic results when used at the same magnifications. These results are significant in that they are provided by an apparatus readily available for use in routine examinations. The portable apparatus of the invention, therefore, is a useful screening tool which encourages performance of colposcopic examinations and thus early diagnosis and treatment. The apparatus of the invention also results in a more time and cost efficient examination and diagnosis.

DESCRIPTION OF DRAWINGS

FIG. 2 is a side view of the portable apparatus of the invention;

FIG. 3 is a top plan view of the apparatus of the invention;

FIG. 4 is a rear view of the apparatus of the invention;

FIG. 5 is a cut-away side view of the apparatus of the invention showing the connection between the main frame lens holder, the light mounting means, the stereoscopic or binocular unit, and a portion of the support system using a single mounting stud element; and FIG. 6 is a side view of a nosepiece suitable for use with the apparatus of the invention.

DETAILED DESCRIPTION OF PRESENTLY PREFERRED EMBODIMENTS

Figure 1:
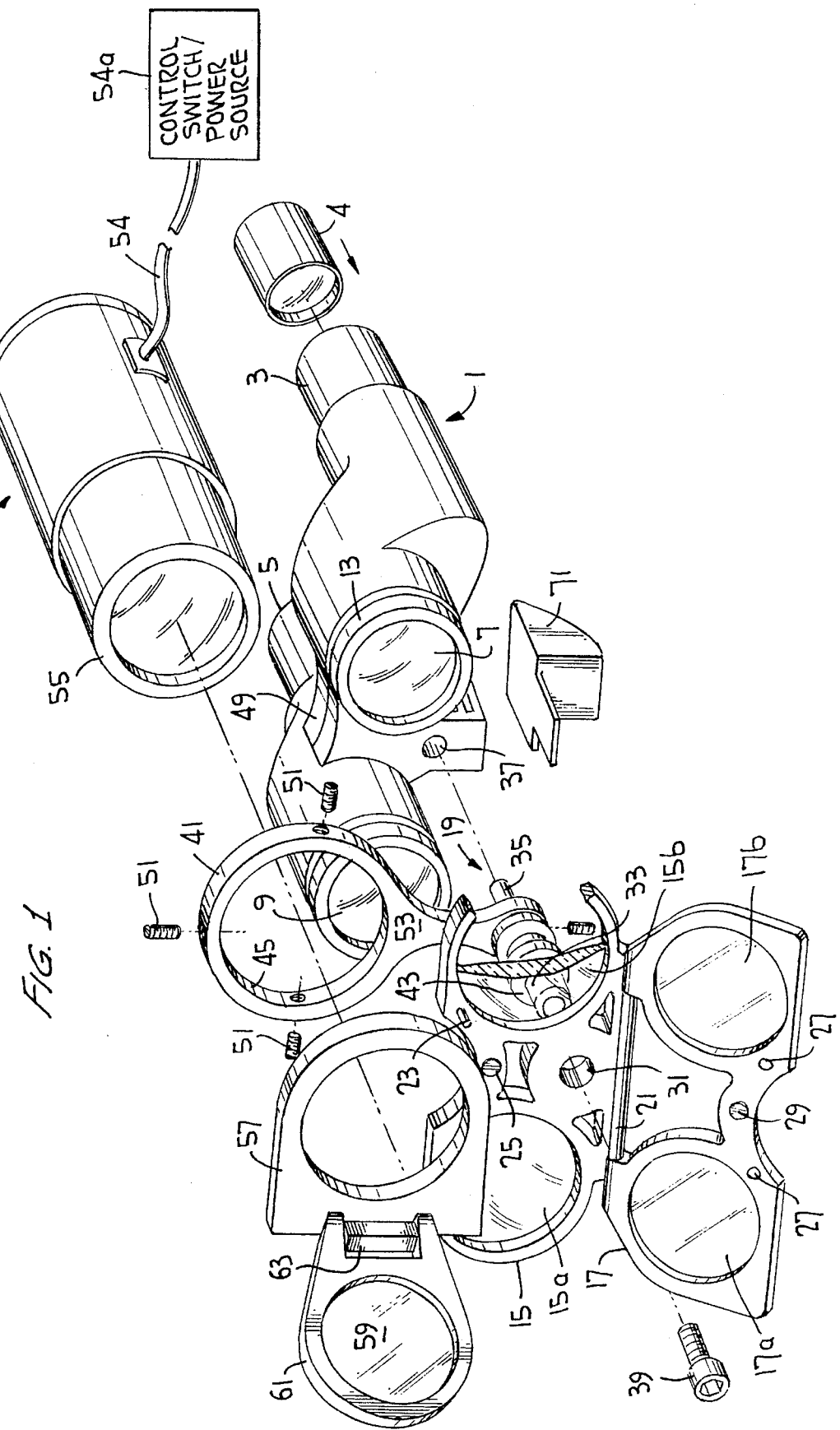
FIG. 1 is an exploded perspective view of the portable apparatus of the invention.

The present invention is directed to a portable apparatus particularly suited for use as a colposcope in conducting close range physical medical examinations. The portable apparatus is particularly useful for this function due to the combination of components as described herein. The portable apparatus is structured to be worn on the face of a user in the manner of eyeglasses. This allows the user to be versatile in positioning and viewing during examination. Further, due to the portable nature of the apparatus, the apparatus is readily available for use regardless of the location of the patient. The patient does not have to be relocated in order to accommodate an examination apparatus, such as with conventional free-standing colposcopes currently commercially available.

The portable apparatus of the invention includes a stereoscopic optical unit or binocular unit 1 which includes two eyepieces 3 and 5 and corresponding viewing lenses 7 and 9, respectively. Within the body of the binocular unit is an S-curve mirror system 11, as shown by dotted lines in FIG. 2, in relation to each eyepiece and corresponding viewing lens. The S-curve mirror system is a conventional mirror system utilized in binocular units. An example of a conventional binocular unit and mirror system which can be utilized in the present invention is commercially sold by Beecher Research Co. under the name "Beecher-Mirage" as described above. While prism systems can function to provide a binocular unit as desired, prism systems are not preferred in portable binocular units due to the weight and bulky nature of the prisms in comparison to mirrors. Present in relation to each viewing lens 7 and 9 is an adjustable focusing element 13 for adjusting the focus of the viewing lens to a particular user's eyesight. Eyepieces 3 and 5 can contain lenses which have been ground to the prescription of the user so that eyeglasses if worn by the user are not required when utilizing the portable apparatus of the invention. The lenses can be incorporated as an integral part of the eyepieces of the binocular unit or included in a detachable lens piece, as shown generally at 4 in FIG. 1, so that different lenses can be utilized with one instrument. The detachable lens piece can include screw threads, a bayonet mount or other conventional attachment means in conjunction with a complementary structure on the eyepieces of the binocular unit for holding the detachable lens pieces in place on eyepieces. In a conventional binocular unit with an S-curve mirror system which provides magnification, distortion is present at short focal lengths and, accordingly, the binocular unit is not useful at magnifications over 6× for close range viewing.

The portable apparatus of the invention is useful for close range physical examinations where precision and accuracy is a requirement, such as in colposcopic examinations. The apparatus of the invention provides a high magnification, preferably 7× and 10× for colposcopic examinations, and adjustment between the magnifications which is consistent and precise. This precision is achieved by providing for repeated fixed placed positioning of the required lenses in relation to the binocular unit, lighting means and filter means. In the present invention, the distortion for the short focal length of the binocular unit is corrected utilizing supplementary lenses 15a and 15b held within a main frame lens holder 15 and an auxiliary frame lens holder 17 which is hingedly mounted at 21 to the main frame lens holder. The main frame lens holder 15 is mounted to viewing lenses 7 and 9 through the use of a mounting stud element 19 which is further described below. The structure of the combined lens holders 15 and 17 insures that the main frame lenses 17a and 17b and auxiliary frame lenses are maintained in a precise fixed position so that proper optical alignment is repeatedly provided in use. To assist in positioning the main frame and auxiliary frame lens holders, at least one locating pin 23 and magnetic element 25 are utilized in conjunction with corresponding holes 27 and a complementary magnetic element 29. In combination with hinge 21, the corresponding locating pins and holes and magnetic elements insure proper alignment and fixed placement of the auxiliary frame lens holder to the main frame lens holder through repeated use.

Additionally providing stability to the apparatus structure is a stud element 19. Present in the main frame lens holder is an opening 31 for receiving a first end 33 of stud element 19. A second end 35 of stud element 19 is positioned in an opening 37 in the binocular unit. A screw or stopper means 39 is used to seal and hold the stud end 33 in place in relation to the main frame lens holder 15.

Additionally utilized in relation to stud element 19 for holding the required components in a required operating relationship to each other is a lamp holder 41. The stem 53 of the lamp holder includes an opening which is used to position the lamp holder 41 on stud element 19 as best shown in FIGS. 1 and 5. Spacing elements 43 are preferably present in relation to mounting stud 19 to hold and stabilize the positions of the respective components in a tight or rigid fixed relationship to each other. The top portion of lamp holder 41 includes an opening 45 for receiving a lamp or light 47. The underside of the light 47 rests in part on top area 49 of binocular unit 1. The lamp holder 41 encircles the lamp and holds the lamp in place by means of set screws 51. Preferably, the top portion of the lamp holder 41 is slightly bendable at stem 53 so that the angle of the light beam provided by the lamp can be focused to coincide with the specific focal point desired. Attached to the light 47 will be a conventional electrical connection 54 to a control switch and/or power source 54a for operating the light. This feature is generally shown in FIG. 1, but for the sake of clarity is not shown in the other figures. A suitable conventional structure includes an electrical connection line attached to an operation switch which in turn is connected to a power source, such as a battery. The switch and power source are preferably in the nature of a battery pack or the like attachable to the clothing of the user. While a light may be provided with a battery as part of the light structure, generally this results in added weight to the unit which is undesirable.

The light beam emitting from end 55 of the light 47 has attached thereto a mounting system for holding a filter. In physical medical examinations, a white light source is provided for illumination purposes. In relation to the light source, in providing colposcopic examinations, a green filter is generally used to better visualize blood vessels in the tissue being examined. The apparatus of the invention allows for the selective use of either a white light source or a green light source. The green light source is provided through the use of a green filter with lamp 47. The mounting system for holding a filter in relation to the light includes a mounting base 57 which is attached to light emitting end 55 of light 47, preferably by encircling end 55. A filter 59 is held within a holder 61 which is hingedly connected by a hinge structure 63 to the mounting base 57. The filter in holder 61, therefore, can rotate into or out of the light beam from light 47 as desired.

The positioning of the main frame and auxiliary frame lens holders, lamp holder, filter mounting system and light in relation to the binocular unit are all combined so that proper optical alignment is provided and maintained through repeated use in physical examinations while also allowing for the selective adjustment of the lenses and light so that variable examination needs can be met.

Further versatility in the use of the apparatus of the invention is provided in that the apparatus is portable and structured for wearing on the face of the user providing the examination in the manner of eyeglasses. This is provided through the use of a support member 65, as best shown in FIGS. 3 and 4, attached to the back side of the binocular unit 1. Preferably, the support means 65 is attached to the binocular unit 1 by attachment to end 35 of stud element 19 using screw 67, as best shown in FIGS. 3 and 4. This reduces the components necessary to assemble the apparatus and exterior space for attachment of components. The support means 65 is rigid and made of a material appropriate to providing support based on the weight of the portable apparatus, i.e., a hard plastic. Attached to support means 65 are a pair of ear prongs 67 and 69 which are positioned on a user's ears in the manner of conventional eyeglasses. To provide further comfort in the use of the apparatus and distribution of weight, a nose piece 71 is provided with the binocular unit. The binocular unit can be provided with a plurality of slots 73 for interchangeably receiving a nose piece 71 as shown in FIG. 6. The replaceable nose piece includes a stem 75 for insertion in one of slots 73 and a cushion portion 77 which will rest upon a nose. Adjustment in location and size of the nose piece is thereby possible in view of the individual using the nose piece.

As a modification to the apparatus as described above, prescription lenses can be provided in relation to eyepieces 3 and 5. Prescription lenses can be mounted or attached to the eyepieces in various manners so that a user by simply re-directing his/her line of sight, and/or slightly adjusting the position of the apparatus, can be provided with regular viewing eyesight without removing the apparatus. This allows for a user to quickly adjust between the magnifying vision utilized during examination and regular vision as used with prescription eyeglasses for the reading of a chart or perspective viewing during the examination. Prescription lenses can be mounted on eyepieces 3 and 5 so that they extend around the eyepieces as shown by lines 79 in FIG. 4 or, alternatively, extend only from the base of the eyepieces as shown by lines 81 in FIGS. 4 and 5. Suitable mounting means are readily determinable by one skilled in the art. The size of the lenses will be sufficient to allow for an alternative line of vision by adjusting one's line of sight or sliding the portable apparatus upon a user's nose so that regular vision can be provided through the additional lenses. The size of the additional lenses, however, necessarily is not so great as to interfere with wearing the apparatus on the face. Depending upon the arrangement which the additional lenses take, an additional stabilizing piece may be required at the nose or the like to provide for good weight distribution of the apparatus.

To provide a colposcopic examination, the lenses in the main frame lens holder and auxiliary lens holder preferably provide magnifications of 7× and 10×, respectively, at short focal lengths. A 7× magnification provides for a working distance of approximately 18 inches, while a 10× magnification provides for a working distance at approximately 12 inches. The lenses are ground to provide the desired magnification in conjunction with the binocular unit 1 and, accordingly, the lenses of the main frame and auxiliary frame holders are also ground to correct the distortion which would be present at a short focal length if only the binocular unit were utilized. Accordingly, the supplementary lenses used with the binocular unit are such so as to adjust the focal length while also providing the desired magnification. Necessarily different magnifications can be provided by the lenses if desired.

The portable apparatus of the invention, therefore, is a compact portable apparatus which is readily usable regardless of the location of a patient thereby providing convenient and ready use of the apparatus. The portable apparatus thus is greatly advantageous for use as a screening tool and will encourage screening and early diagnosis since the apparatus is more economical and available for use as compared to conventional free-standing colposcopes. The portable apparatus of the invention has been utilized in studies to compare the portable apparatus with a conventional free-standing colposcope in the examination of patients. Substantially equivalent results were obtained between the portable apparatus and a conventional colposcope at the same magnifications. Conventional loupes as utilized in surgical procedures are inadequate for use in examinations which require high magnification since loupes only provide one fixed magnification, for example of 8× or less, and are not structured to readily provide alternative magnifications or to be used with a light or filter means. If a higher magnification were used in the loupes, distortion would be present making them useless for close range physical examinations, such as colposcopic examinations. Loupes only provide for limited fixed magnification along a short focal length. Accordingly, conventional loupes are unsuitable for long term use in close range physical examinations. The present invention provides for a binocular unit with two mirror systems which are used in conjunction with auxiliary lenses to provide for varied magnified vision at a non-distorted short focal length, and also in particular in conjunction with a light and filter means.

As will be apparent to one skilled in the art, various modifications can be made within the scope of the aforesaid description. Such modifications being within the ability of one skilled in the art form a part of the present invention and are embraced by the appended claims.

It is claimed:

1. A portable close-range examination apparatus comprising a stereoscopic optical unit having a pair of viewing lenses and corresponding eyepieces with a mirror system positioned between each viewing lens and corresponding eyepiece; a main frame lens holder attached to the viewing lenses of said stereoscopic optical unit for holding a first pair of lenses which provide a first magnification at an undistorted short focal length; an auxiliary frame lens holder hingedly connected to said main frame lens holder for containing a second pair of lenses which in combination with said first pair of lenses provides a second magnification at an undistorted short focal length, said second magnification being greater than said first magnification; a light means for providing a light beam; a filter mounting means with a filter means hingedly connected thereto, said filter mounting means being attached to an end of said light means through which a light beam is emitted; a mount means for holding said light means; a stud element for rigidly interconnecting at least said stereoscopic optical unit, said main frame lens holder and said mount means; and a support means constructed and arranged to support said apparatus in use by a user of said apparatus in the manner of eyeglasses.

2. A portable apparatus as claimed in claim 1 wherein said first pair of lenses provide a magnification of 7× at an undistorted short focal length.

3. A portable apparatus as claimed in claim 1 wherein said second pair of lenses provides a magnification of 10× at an undistorted short focal length.

4. A portable apparatus as claimed in claim 1 wherein said mount means for holding said light means is bendable to allow for angling of said light beam.

5. A portable apparatus as claimed in claim 1 wherein said stereoscopic optical unit includes prescription lenses in said eyepieces.

6. A portable apparatus as claimed in claim 5 wherein a prescription lens is mounted adjacent each eyepiece.

7. A portable apparatus as claimed in claim 1 wherein the filter means includes a green filter.

8. A portable apparatus as claimed in claim 1 wherein a prescription lens is mounted adjacent each eyepiece.

9. A portable apparatus according to claim 1 wherein said main frame lens holder and said auxiliary frame lens holder having complementary fastening means for fixedly holding said auxiliary frame lens holder in an abutting relationship to said main frame lens holder so that optical alignment is provided between said first pair of lenses and said second pair of lenses.

\* \* \* \* \*